(12) United States Patent
Davies et al.

(10) Patent No.: US 7,258,661 B2
(45) Date of Patent: Aug. 21, 2007

(54) STOMA PLUG

(75) Inventors: Geraint Davies, Cambridge (GB); John Cline, New Brunswick, NJ (US); Christopher C. Gregory, Newtown, PA (US); Alan Cucknell, Cambridge (GB); Julian Scarfe, Cambridge (GB); Pete Cauwood, Cambridge (GB)

(73) Assignee: Bristol-Myers Squibb Company, New York, NY (US)

( * ) Notice: Subject to any disclaimer, the term of this patent is extended or adjusted under 35 U.S.C. 154(b) by 117 days.

(21) Appl. No.: 10/939,846

(22) Filed: Sep. 13, 2004

(65) Prior Publication Data

US 2006/0058576 A1    Mar. 16, 2006

(51) Int. Cl.
*A61F 2/02* (2006.01)

(52) U.S. Cl. .................. 600/32; 623/14.13; 600/29; 600/30; 600/31

(58) Field of Classification Search ............ 600/29–32; 604/332–343; 128/DIG. 25, 897–898, 887
See application file for complete search history.

(56) References Cited

U.S. PATENT DOCUMENTS

| | | | |
|---|---|---|---|
| 3,841,304 A | 10/1974 | Jones | |
| 3,854,469 A | 12/1974 | Giori et al. | |
| 4,552,128 A | 11/1985 | Haber | |
| 4,950,223 A * | 8/1990 | Silvanov | 600/32 |
| 5,045,052 A | 9/1991 | Sans et al. | |
| 5,090,424 A * | 2/1992 | Simon et al. | 128/885 |
| 6,071,268 A * | 6/2000 | Wagner | 604/332 |
| 6,096,057 A * | 8/2000 | Klingenstein | 606/197 |
| 2003/0181879 A1* | 9/2003 | Mulhauser et al. | 604/332 |
| 2004/0260257 A1* | 12/2004 | Ciok et al. | 604/332 |

FOREIGN PATENT DOCUMENTS

| | | |
|---|---|---|
| DE | 2431888 A1 | 1/1976 |
| EP | 1348411 A1 | 10/2003 |
| WO | WO89/00030 | 1/1989 |
| WO | WO90/07311 * | 7/1990 |

* cited by examiner

*Primary Examiner*—Charles A. Marmor, II
*Assistant Examiner*—Sara Lustusky
(74) *Attorney, Agent, or Firm*—Stuart E. Krieger (57) ABSTRACT

An ostomy plug is described comprising first and second chambers having adjacent ends coupled to, and in fluid communication with, each other. The first chamber may be for insertion into a stoma. The second chamber may contain fluid for inflating the first chamber when the second chamber is squeezed or otherwise compressed. The plug may have a figure-of-eight configuration. The plug may be configured to permit venting of flatus while obstructing escape of other body waste from the stoma. The plug may incorporate an insertion aid for aiding insertion into a stoma. The plug may also incorporate a device for regulating the inflation pressure of the fluid to avoid undesirably high inflation pressures in the stoma.

66 Claims, 7 Drawing Sheets

STOMA PLUG

FIELD OF THE INVENTION

The present invention may relate to the field of stoma plugs, for insertion at least partly into a patient's stoma for plugging the stoma. One aspect of the invention may relate to an inflatable stoma plug.

BACKGROUND TO THE INVENTION

The creation of an ostomy (stoma) is the therapy for many sufferers of diseases or injury of the gastrointestinal or urinary tract. An ostomy is the rerouting of the tract through the abdominal wall to outside the patient's body. Once a stoma has been created, the patient must, usually for the rest of his or her life, use a device worn on the body for capturing or containing the body waste. This has traditionally been done with a bag or pouch attached to the body with adhesive patches or constricting belts. However, the wearing of such a pouch can be an extremely embarrassing and belittling experience for many ostomates. A pouch requires significant changes in public and personal activities.

A stoma plug offers the potential for an ostomate to return to some form of normality. The plug is used to block the stoma, in order to store body waste temporarily inside the tract. The plug is removable manually when the ostomate desires to discharge the body waste.

U.S. Pat. No. 4,950,223 describes an inflatable ostomy plug including a movable bellows located above a plate, and an inflatable bell-shaped bung below the plate. The inflatable bung is separate from the bellows and is mounted on a sliding inflation tube that moves with the bellows. The inflation tube extends through a sliding seal in the plate. In use, the ostomate can inflate the bung by compressing the bellows, which also causes the inflation tube to descend, thereby inflating the bung away from the bellows. The bung is deflated by an opposite movement of the bellows, which also causes the sliding tube to ascend with respect to the sliding seal.

Although the idea of an inflatable plug is highly appealing in theory, the plug described in U.S. Pat. No. 4,950,223 has significant potential disadvantages. Firstly, when the plug is inflated, the inflation tube is positioned substantially inside the stoma. The presence of such a relatively stiff tube inside the stoma may be undesirable in terms of safety for the ostomate. Secondly, it is not possible to vent flatus while the bung is inflated in the stoma. Flatus can only be vented when the bung is collapsed to allow discharge of body waste from the stoma. This presents severe limitations for the ostomate, because the ostomate will have to collapse the bung very frequently in order to avoid an uncomfortable accumulation of flatus within the body. Finally, the design of the plug is very complicated and therefore expensive, and the sliding seal may be prone to leakage of fluid. A leakage of fluid reduces the sealing pressure in the bung, and hence reduces the effectiveness of the plug.

SUMMARY OF THE INVENTION

Broadly speaking, the invention may provide an ostomy plug comprising a first chamber and a second chamber. The chambers may be in fluid communication with each other. The first chamber may function as an inflatable bung insertable into a stoma. The second chamber may function as an inflation device for the first chamber.

The invention may further comprise one of more of the following optional features:

(a) The plug may be configured to permit the venting of flatus while the plug is in deployed condition for obstructing the discharge of solid and/or semi-solid and/or liquid body waste. For example, flatus may be vented:
  (i) around the exterior of the plug at the interface between the plug and the stomal wall; and/or
  (ii) via one or more vent channels or passages provided within the plug.

(b) One or more external or internal surfaces of the plug may be configured to aid the venting of flatus therepast, while obstructing the escape of other body waste.

(c) The first and second chambers may be coupled end-to-end at a mutual junction region. A fluid communication path between the chambers may be between a first region in the first chamber at or near the junction region, and a second region in the second chamber at or near the junction region.

Such a structure may provide a simple, yet highly effective arrangement of chambers, without an undesirable long and/or rigid connection tube between the chambers.

(d) A one-way valve may be included in a fluid communication path between the fluid communication chambers. The one-way valve may be configured to admit fluid for inflating the first chamber, but to obstruct fluid leaving the first chamber. The one-way valve may be configured to be deactivateable by external manipulation of the valve.

(e) The second chamber may be detachable from the device once the first chamber has been inflated. The second chamber may be re-attachable, or the detachment may be permanent (e.g. by breaking a frangible connection). A valve (e.g., the one-way valve mentioned above) may be provided for closing the first chamber to prevent escape of the inflation fluid from the first chamber.

(f) The plug may comprise a plurality of concentrically arranged chambers. For example, a third chamber may be disposed around at least a part of the first chamber and/or a fourth chamber may be disposed around at least a part of the second chamber. The third chamber may be in fluid communication with the fourth chamber. Such a plurality of concentrically arranged chambers may enable different sealing pressures to be used for different regions of the plug. A plurality of concentrically arranged chambers may also enable different surface coatings and textures to be used for different regions of the plug.

(g) The plug may comprise a surface portion with a non-smooth surface texture. The surface portion may be a portion that engages a stoma wall in use. The non-smooth surface portion may be configured according to one or more of:
  (i) To aid venting of flatus;
  (ii) To obstruct passage of solid and/or semi-solid and/or liquid body waste therepast;
  (iii) To aid frictional engagement with the stomal wall;
  (iv) An embossed surface texture of at least one valley and/or at least one ridge;
  (v) A microstructure;
  (vi) At least one projecting rib and/or flap.

(h) The plug may carry, over at least a portion of a surface thereof, a coating comprising one or more of:

(i) A lubricant;
(ii) A hydrophobic material;
(iii) A hydrophilic material;
(iv) An adhesive.
(i) The first chamber of the plug may have a convex configuration. Such a configuration may facilitate venting of flatus and/or aid insertion of the first chamber into the stoma.
(j) The first and second chambers of the plug may together define a figure-of-eight configuration. One of the chambers may be deflated or at least partly deflated, and so the figure of eight configuration might not always be apparent. Nevertheless, such a configuration may apply to the shape(s) of the chambers when each is in the inflated condition.
(k) The plug may be incorporated into, associated with, or accompanied by, an insertion means. The insertion means may be configured to aid or facilitate delivery of the first chamber into the stoma.

For example, the insertion means may consist of a tube, or sleeve, or other support (e.g. having a passage or recess therein) that may be presented to the stoma opening but preferably not inserted into the stoma. The first chamber may be inverted and stored inside the insertion means, and/or it may be inverted and stored inside the second chamber. In this deflated and stowed condition of the first chamber, the first chamber may not project significantly from the insertion means, which may thereby allow the insertion means to be presented against the stoma. Squeezing the second chamber may displace the first chamber through the insertion means and into the stoma.

(l) The plug may incorporate a means for regulating the inflation pressure of the first chamber. The regulating means may be configured to prevent over-inflation of the first chamber, since the tissue comprising the stoma and bowel may be sensitive to pressure. It may be important that inflation pressure not exceed local capillary pressure to prevent necrosis of mucosal tissue. For example, the regulation means may comprise one or more of:
(i) A pressure relief valve that opens when pressure in the second chamber reaches a pre-set value, thereby preventing further inflation of the first chamber.
(ii) A valve between the first and second chamber that closes when pressure in the second chamber exceeds a pre-set value, thereby preventing further inflation of the first chamber
(iii) A valve between the first and second chamber that closes when pressure in the first chamber exceeds a pre-set value, thereby preventing further inflation of the first chamber
(iv) Rupture of the second chamber, or rendering it incapable of holding internal pressure, when pressure in the second chamber reaches a preset value, thereby preventing further inflation of the first chamber
(v) A cap which holds the device against the wearer's peristomal area, either directly or indirectly via an ostomy wafer or additional appliance. The cap may hold the second chamber in a compressed state, thereby keeping the first chamber inflated. The cap could incorporate a means of applying a pre-set force (such as a spring) to the second chamber to ensure the appropriate pressure in the first chamber.

Further features and advantages of the invention will be apparent from the following detailed description. Although certain significant features have been described above and in the appended claims, the Applicant claims protection for any novel feature or idea described herein and/or illustrated in the drawings, whether or not emphasis has been placed thereon.

BRIEF DESCRIPTION OF THE DRAWINGS

Non-limiting preferred embodiments of the invention are now described, by way of example, with reference to the accompanying claims and drawings, in which:

DETAILED DESCRIPTION OF PREFERRED EMBODIMENTS

Figure 1:
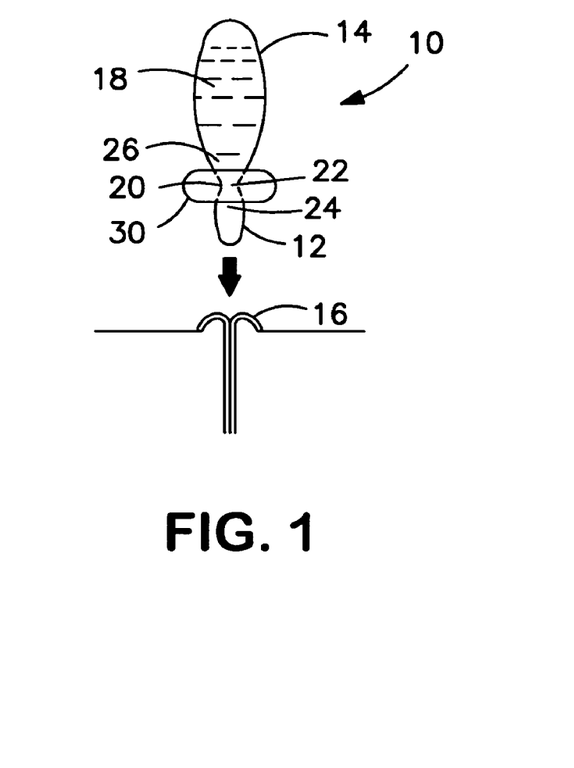
FIG. 1 is a schematic cross section through an ostomy plug of a first embodiment, shown in a non-deployed condition.
Figure 2:
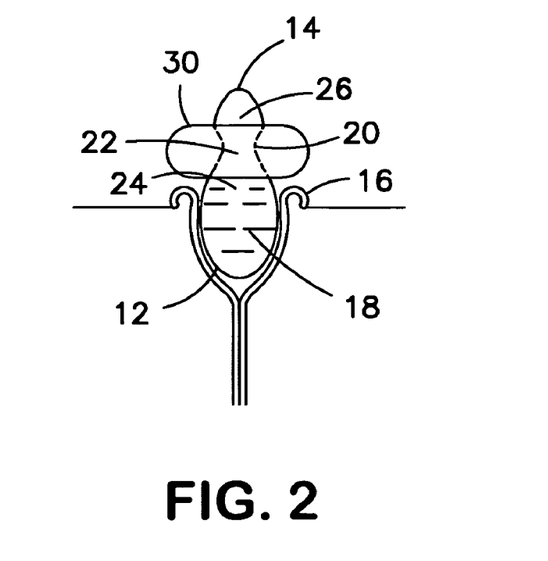
FIG. 2 is a schematic cross section showing the ostomy plug of FIG. 1 in a deployed condition.

Referring to FIGS. 1 and 2, an ostomy plug 10 may be illustrated for at least partial insertion into a patient's stoma 16, for plugging the stoma 16. The ostomy plug 10 may be configured to obstruct the passage of solid and/or semi-solid and/or liquid body waste when the plug 10 is in a deployed condition. The ostomy plug 10 may be configured to allow venting of flatus through and/or around the plug 10 even in the deployed condition of the plug 10.

The plug 10 may comprise a first chamber 12 and a second chamber 14. The first chamber 12 may be in fluid communication with the second chamber 14. The first chamber 12 may be configured as an inflatable bung for at least partial insertion into the stoma 16. The second chamber 14 may be configured as an inflation driver for supplying fluid to inflate the first chamber 12. The first and second chambers 12 and 14 may together contain a predetermined amount of inflation fluid 18 which may be less than the combined maximum internal volumes (e.g., capacities) of the chambers 12 and 14. In a non-deployed condition (FIG. 1), the first chamber 12 may be substantially deflated and at least a substantial portion (if not all) of the fluid 18 may be in the second chamber 14. In the non-deployed condition, the deflated first chamber 12 may easily be fed into the stoma 16 with little or no difficulty, nor discomfort. Moreover, in the deflated condition, there may be no risk of frictional damage to the sensitive tissue of the stoma 16 as the first chamber 12 is inserted.

The plug 10 may be brought to its deployed condition (FIG. 2) by manipulating the second chamber 14 to reduce the volume of the second chamber 14, in order to drive the inflation fluid 18 into the first chamber 12 for inflating the first chamber 12. The second chamber 14 may be manipulated, for example, by squeezing and/or pressing and/or squashing the second chamber 14. During inflation of the first chamber 12, the contact between the first chamber 12 and the internal stoma wall may be of an at least partial (or predominantly) rolling nature, instead of sliding contact. Such rolling contact may further reduce the risk of frictional damage of the sensitive stoma tissue. In the inflated state of the first chamber 12, the first chamber 12 fills the tract in the region of the stoma 16, in order to reliably block discharge of liquid and/or solid body waste.

As illustrated in more detail in later embodiments, the plug 10 may be configured with an inflation-retention device or arrangement to retain the inflation fluid 18 in the first chamber 12 and/or to retain the second chamber 14 deflated, once the first chamber 12 has been inflated. The inflation-retention device or arrangement may be selectively releasable or deactivatable, in order to allow the first chamber 12 to be deflated when the ostomate desires to remove the plug 10. Alternatively, the ostomate may puncture the plug, to deflate the first chamber 12.

The inflation fluid 18 may be any suitable fluid, for example, liquid (e.g., saline), gel (e.g., a viscous gel) or gas. The inflation fluid 18 may be body-compatible, as an additional safety measure in the unlikely event that the fluid 18 may leak from the plug 10 accidentally.

The first and second chambers 12 and 14 may have any of a wide variety of shapes. The first and second chambers 12 and 14 may have the same (or at least similar) shapes, or the shapes may be different. The first and second chambers 12 and 14 may be made of the same material or different materials. Suitable materials may include olefin films, multilayer films incorporating a barrier layer with high resistance to gas and/or fluid transmission, thermoplastic elastomer, or silicone rubber. One or both of the chambers may be made of a resilient material. The first and second chambers 12 and 14 may have the same (or at least similar) internal volumes (e.g., capacity), or the internal volumes may be different.

In the present embodiment, at least one of the first and second chambers 12 and 14 may have a generally rounded and/or convex and/or lobed profile. For example, the first chamber 12 may be lobed. Such a shape may encourage flatus to vent around the sides of the first chamber 12.

The first and second chambers 12 and 14 may be joined end-to-end at a junction region 20. A fluid communication path 22 between the first and second chambers 12 and 14 may be between a first portion 24 of the first chamber 12 near or at the junction region 20, and a second portion 26 of the second chamber 14 near or at the junction region 20. Such a configuration of the chambers 12 and 14 joined together, with a relatively short fluid communication path from one to the other, can avoid the need for a relatively rigid, long inflation tube between the chambers 12 and 14.

The junction region 20 may be configured as a waist or neck that has a transverse dimension smaller than a corresponding maximum transverse dimension of at least one of the first and second chambers 12 and 14. In the present embodiment, the junction region 20 may be configured as a waist that is smaller than the maximum transverse dimension(s) of both the first and second chambers 12 and 14, to thereby define a figure-of-8 type configuration. The term maximum transverse dimension may refer to the dimension when the respective chamber is inflated.

The plug 10 may be generally symmetrical so that it may be used in either orientation (e.g., the first and second chambers 12 and 14 may substantially identical or similar, so that either chamber may constitute the chamber for insertion into the stoma 16). Alternatively, the plug 10 may have a predetermined orientation in which it is intended to be used.

The plug 10 may further comprise a collar 30 located at or near the junction region 20. The collar 30 may be substantially stiff, or it may be flexible but more stiff than the first and second chambers 12 and 14. The collar 30 may be resilient. A function of the collar 30 may to provide shape support for the first and second chambers 12 and 14. Another function of the collar 30 may be to act as a stop to limit the extent of insertion of the plug 10 into the stoma 16 (as best seen in FIG. 2). Another function of the collar 30 may be to enable the collar 30 to be removably attached (e.g., by an adhesive or mechanical coupling) to another part of an ostomy appliance (as illustrated in later embodiments).

Figure 3:
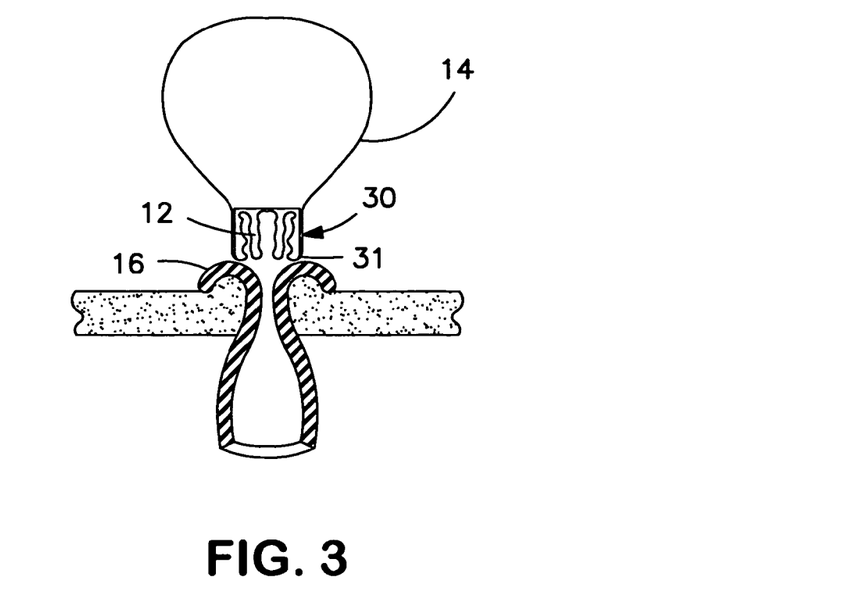
FIG. 3 is a schematic cross section through a second embodiment of ostomy plug in a non-deployed condition and including an insertion aid member.
Figure 4:
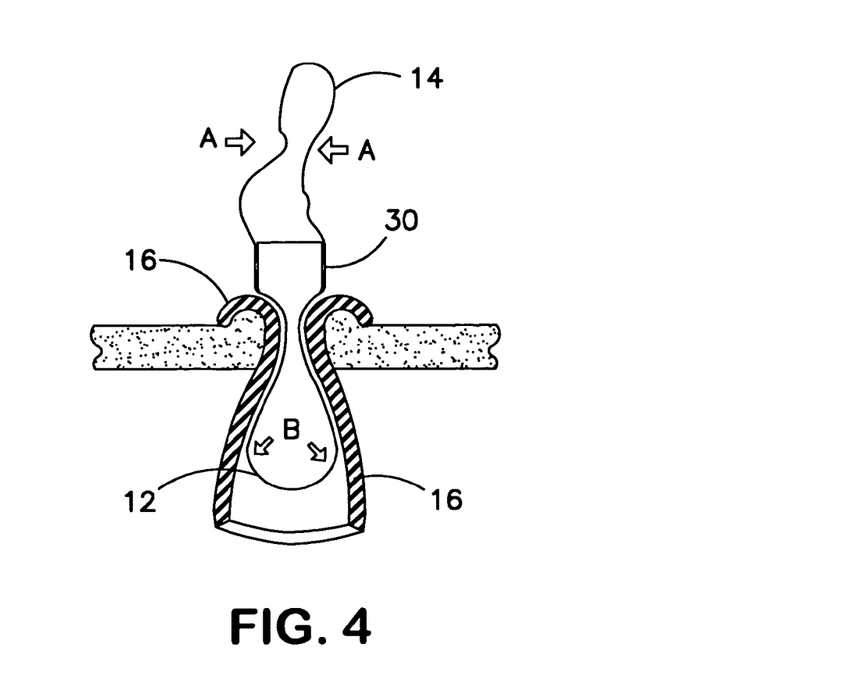
FIG. 4 is a schematic cross section showing the second embodiment in a deployed condition.
Figure 5:
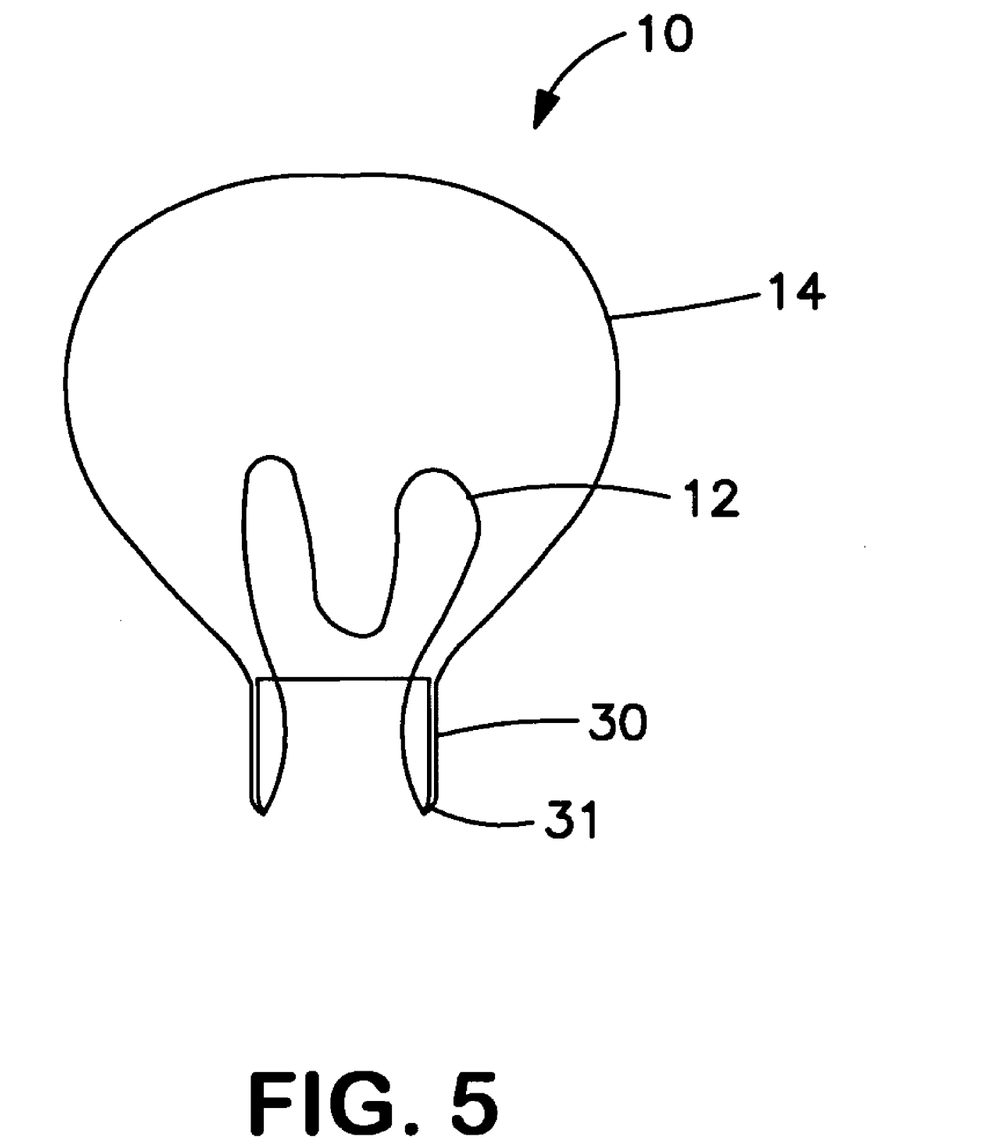
FIG. 5 is a schematic cross section through a third embodiment of ostomy plug similar to the second embodiment.

Referring to FIGS. 3-5, another function of the collar 30 may be to act as an insertion aid (insertion means or insertion member) for the plug, to guide the first chamber into the stoma opening during inflation. The collar 30 may be shaped as a tube or sleeve. The collar 30 may be dimensioned so that it can be presented to, but does not substantially enter, the stoma 16. The collar 30 may have a proximal end 31 that is slightly inwardly tapered, so as to guide the first chamber 12 into the stoma 16 as the first chamber 12 is inflated.

As may be seen in FIG. 3, prior to first use, the first chamber 12 in its deflated condition may be stowed (at least partly or at least predominantly) in the collar 30. The first chamber 12 may be inverted and folded on its self so as to fit within the collar 30. Alternatively, as depicted in FIG. 5, the first chamber 12 may be inverted and stowed (at least partly, or at least predominantly) in the second chamber 14. In FIG. 5, some of the detail of FIG. 3 is omitted for the sake of brevity. In either case, in the initial stowed condition of the first chamber 12, the first chamber 12 does not project significantly from the collar 30. This allows the collar 30 to be presented directly against the stoma 16 when the user desires to fit the plug into the stoma 16.

Referring to FIG. 4, when the second chamber 14 is squeezed or compressed (for example, as indicated by arrows "A"), the inflation fluid may drive the first chamber 12 through the collar 30 and into the stoma 16 (as indicated by arrows "B"). The size of the collar 30 and/or the tapered end 31 of the collar 30 may guide the emerging first chamber 12 so that the first chamber 12 is directed surely into the stoma 16. The user may hold the collar 30 manually against the stoma 16 during the inflation, or the collar 30 may be supported directly or indirectly by another device, for example, an adhesive wafer 50 illustrated later. During inflation, the emerging first chamber 12 may exhibit the same rolling contact with the stomal tissue as described above. Such rolling contact may reduce the risk of frictional damage to the stomal tissue. Therefore, it may be seen that the insertion member 30 may provide a convenient means for inserting the first chamber 12 into the stoma 16, as well as a device for protecting the first chamber 12 prior to inflation.

In any of the constructions described herein, the outer wall surface (or at least a portion thereof) of at least the first chamber 12 may optionally have a coating and/or a surface structure (e.g. a microstructure) to aid (i) insertion into the stoma 16; and/or (ii) fixation within the stoma 16; and/or (iii) escape of flatus between the interface between the first chamber 12 and the stomal tissue; and/or (iv) obstruction of solid, semi-solid and liquid body waste. Such features may be implemented by one or more of:

(a) A lubricant coating;
(b) A hydrophobic coating;
(c) A hydrophilic coating;
(d) Miniature pathways provided on the surface of the first chamber 12 to provide channels for escape of flatus up and out of the stoma. The pathways may be tortuous to obstruct solid and liquid matter from escaping. The pathways may be in the form of ridges and valleys. The pathways may be defined by an embossed surface configuration.
(d) Protruding flexible flaps and/or ribs located on the wall of the first chamber 12 so as to engage the stomal wall. The flexible flaps/ribs may be located on a "belly" or mid-region of the first chamber 12. The flexible flaps/ribs may be formed as a microstructure. The flexible flaps/ribs may create numerous successive seals against the stomal wall.
(e) A generally contoured surface shaped to encourage frictional hold.
(f) A weak adhesive. The adhesive may provide a bond to the stomal wall that obstructs escape of solid, semi-solid and liquid body waste, but that is sufficiently weak to allow the first chamber 12 to be deflated and withdrawn from the stoma 16 without damaging the stomal wall tissue.

Figure 6:
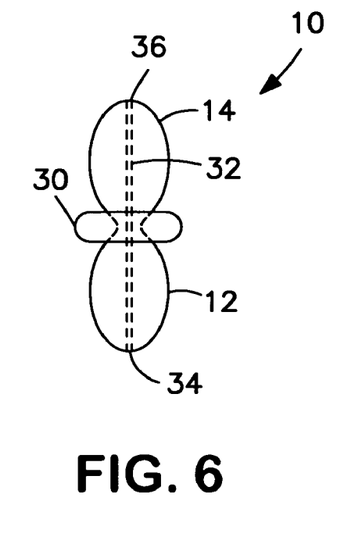
FIG. 6 is a schematic cross section showing a fourth embodiment of ostomy plug (in a schematic expanded profile) and including a flatus vent.

Referring to FIG. 6, the plug 10 may comprise or further comprise a flatus vent passage 32. The passage 32 may be defined by a conduit extending from a first aperture 34 in the first chamber 12 through the plug 10 to a second aperture 36 in the second chamber 14. The first aperture 34 may be at or near an extremity of the first chamber 12 remote from the junction region 20. The second aperture 36 may be at or near an extremity of the second chamber 14 remote from the junction region 14. The passage 32 may be configured such that it is flexible, in order to avoid a rigid tube extending inside the stoma 16. The passage 32 may be configured such that the passage 32 is substantially non-collapsing when subjected to the inflation pressure inside one or both of the chambers 12 and 14. Alternatively, the passage 32 may be at least partly collapsing, but may open under the pressure of flatus to allow the flatus to escape. The passage 32 may be an open channel, or it may contain a filling (not shown). The filling may carry or comprise a malodour counteractant (e.g., an odour absorber, an odour masker, or an odour reactant). An example malodour counteractant may be activated or non-activated charcoal. Additionally, or alternatively, the filling may serve to resist collapsing of the passage 32 and/or to resist escape of liquid body waste through the passage 32.

Figure 7:
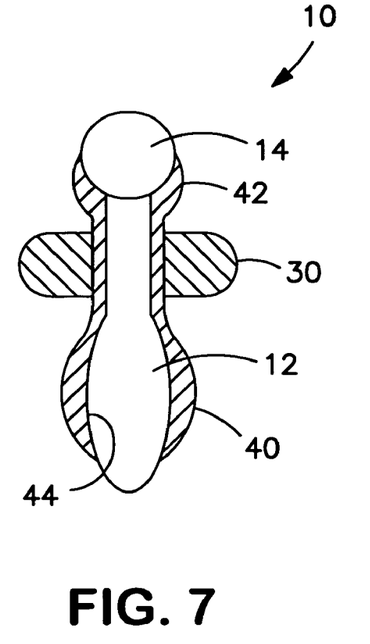
FIG. 7 is a schematic cross section showing a fifth embodiment of ostomy plug (in a schematic expanded profile) and including concentric chambers.

Referring to FIG. 7, the plug 10 may comprise a plurality of chambers. The chambers may be arranged concentrically. For example, the plug 10 may comprise a third chamber 40 concentrically around at least a part of the first chamber 12, and a fourth chamber 42 concentrically around at least a part of the second chamber 14. The third and fourth chambers 40 and 42 may be in fluid communication with each other, in a similar manner to the first and second chambers 12 and 14. Using such plural concentric chambers may enable a combination of different inflation pressures to be used for different parts of the plug 10. For example, the third chamber 40 may be inflated to a smaller, or greater, pressure than the first chamber 12. Different sealing pressures may provide advantages in terms of comfort and seal performance. Additionally or alternatively, the concentric chambers may be used to provide different surface characteristics, again to provide advantages in terms of comfort and seal performance. The concentric chambers may have different extents from one another, so that an outer chamber (e.g., the third chamber 40) covers a portion of an inner chamber (e.g., the first chamber 12), leaving another portion of the inner chamber exposed or uncovered.

An interface 44 between the concentric chambers may be sealed to prevent completely the passage of even gas (e.g., flatus) along the interface. Alternatively, the interface 44 may embody a flatus vent passage 32 as described previously. Implementing a flatus vent passage 32 using the confronting walls of the chambers 12, 14, 40 and 42 may be more straightforward than implementing a dedicated conduit through the first and second chambers 12 and 14. The confronting surfaces of the chamber walls may include any of the aforementioned coatings, seals and textures for allowing venting of flatus therebetween while obstructing escape of solid and/or semi-solid and/or liquid body waste.

Figure 8:
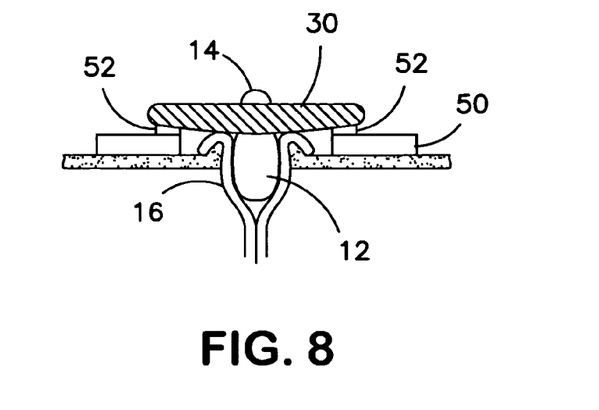
FIG. 8 is a schematic cross section showing a sixth embodiment of ostomy plug including a body attachment wafer.

Referring to FIGS. 2 and 4, the plug 10 in its deployed condition may be retained in the stoma by frictional engagement between the inflated first chamber 12 and the stoma walls. Additionally, or alternatively, an attachment device may be used to attach the plug 10 to the body. For example, referring to FIG. 8, the attachment device may comprise an adhesive wafer 50 worn on the body. The wafer 50 may comprise a mechanical or adhesive coupling 52 for co-operating with the collar 30 in order to retain the plug 10 in position. The coupling 52 may be releasable and/or separable. Additionally or alternatively, other attachment devices, for example, a belt (not shown) may be used to retain the plug 10 relative to the stoma 16.

Figure 9:
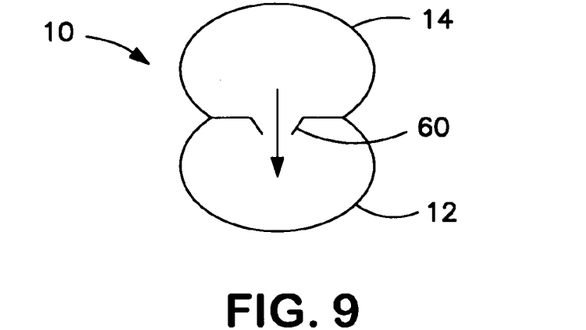
FIG. 9 is a schematic cross section showing a seventh embodiment of ostomy plug including a non-return valve.

Referring to FIG. 9, the plug 10 may optionally include a one-way fluid communication valve 60 between the first and second chambers 12 and 14. The valve 60 may be an inflation-retention device for the first chamber 12. The valve 60 may be a non-return valve. The valve 60 may permit fluid to be driven from the second chamber 14 to the first chamber 12, but may obstruct fluid flowing back from the first chamber 12 to the second chamber 14. The valve 60 may be manipulable to permit the fluid to flow back to the second chamber 14, for example, by squeezing or deforming the valve 60 from its normal shape. Such an arrangement can maintain reliable inflation of the first chamber 12, but permit controlled deflation of the first chamber 12 when desired by the ostomate.

Figure 10:
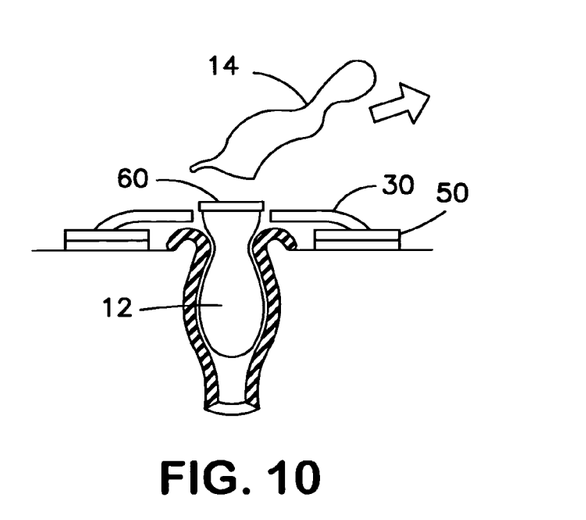
FIG. 10 is a schematic cross section showing an eighth embodiment of ostomy plug including a detachable chamber.

Referring to FIG. 10, the second chamber 14 may be detachable from the plug 10 once the first chamber 12 has been inflated. In the embodiment of FIG. 10, the first chamber 12 (with the optional collar 30) may be supported by an adhesive wafer 50. The second chamber 14 may be detached from the first chamber 12 and the wafer 50. For example, the second chamber may be permanently detached by breaking a frangible attachment. Alternatively, the second chamber 14 may be re-attachable by means of a re-attachable fluid-tight coupling (not shown). The embodiment of FIG. 10 may also include the non-return valve 60 described previously in order to retain inflation pressure in the first chamber 12 once the second chamber 14 has been detached.

Figure 11:
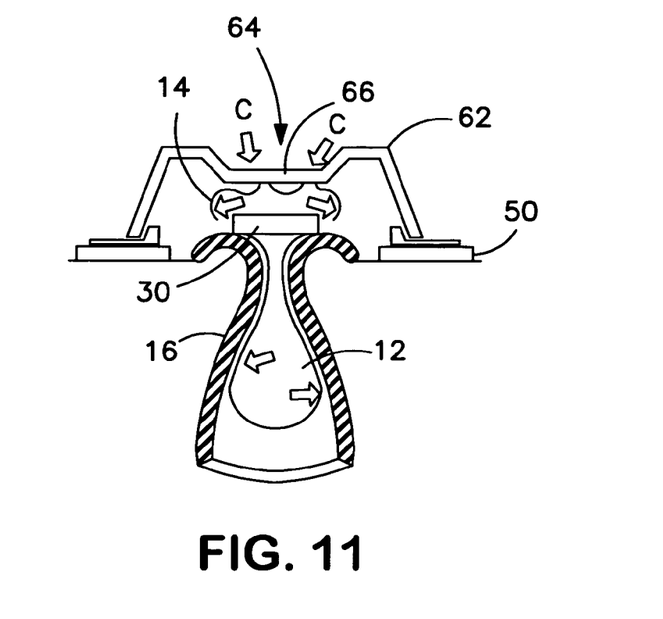
FIG. 11 is a schematic cross section showing an ninth embodiment of ostomy plug including a cover.

Referring to FIG. 11, a cover (e.g. a cap) 62 may be used over the second chamber 14. The cover 62 may be permanently or removably secured to the second chamber 14. The cover 62 may function as an inflation-retention device for the first chamber 12. The cover may be fastenable in a deployed position (as shown in FIG. 11) over the deflated second chamber 14, in order to maintain the second chamber 14 in a deflated, collapsed condition. Such a condition may prevent fluid from flowing back into the second chamber 14. The cover 62 may be fastenable in the deployed position to the collar 30 and/or to the adhesive wafer 50 (if used). The cover 62 may be fastened by a releasable adhesive or mechanical coupling. The cover 62 may comprise a deodorising filter 64 for filtering flatus venting through or around the plug 10.

The cover 62 may additionally or alternatively function as, or carry, an inflation pressure regulator 64, for regulating the inflation pressure of the fluid within the plug. The stomal tissue may be sensitive to pressure. In particular, it may be important that the inflation pressure not exceed local capillary pressure to prevent necrosis of mucosal tissue. For example, the pressure relief regulator 64 may comprise a compression device 66 for generating a pre-set compression force against the second chamber 14 (as indicated by arrows "C"). The pre-set compression force may control the pressure in the first chamber 12, during application of the device and/or during the entire wear period. The compression device 66 may be a portion, e.g. a resilient portion, of the cover 62. Alternatively, the compression device 66 may include a resilient member (not shown), such as compressible foam or a spring, for applying a predetermined compression force.

Figure 12:
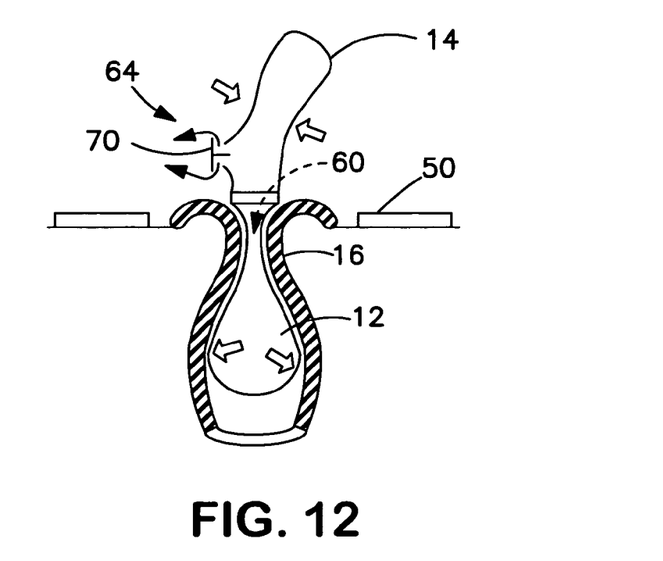
FIG. 12 is a schematic cross section showing a tenth embodiment of ostomy plug including a pressure relief valve.
Figure 13:
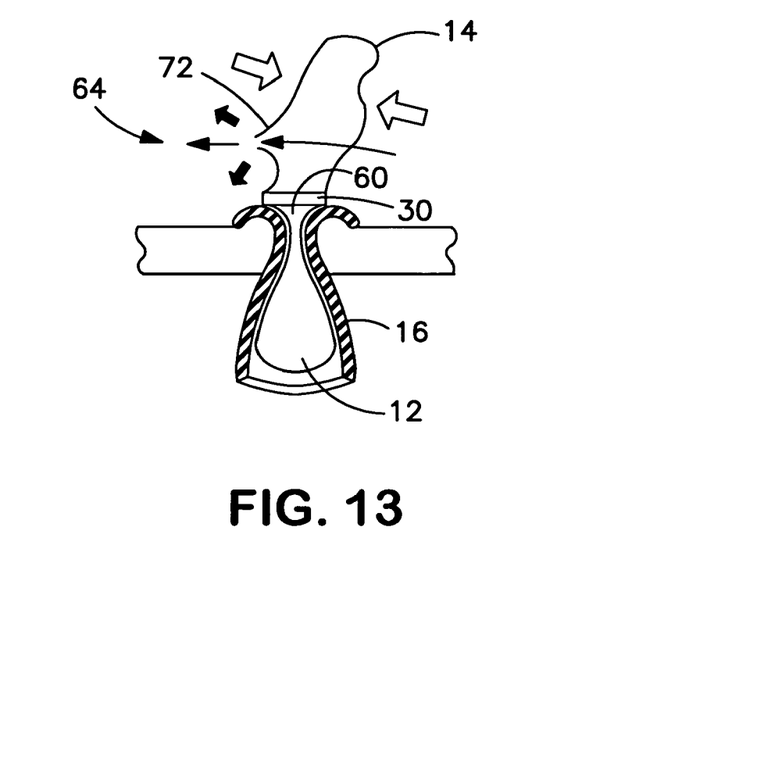
FIG. 13 is a schematic cross section showing an eleventh embodiment of ostomy plug including a rupturable vent portion.
Figure 14:
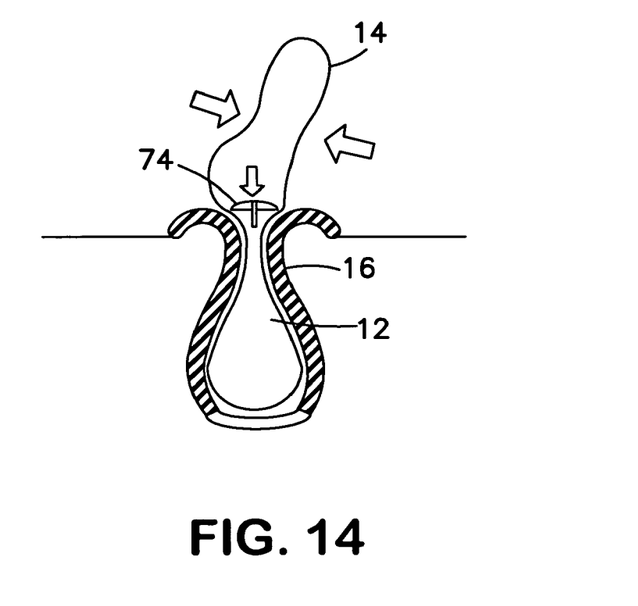
FIG. 14 is a schematic cross section showing a twelfth embodiment of ostomy plug including a stop valve.

The further embodiments of FIGS. 12-14 may illustrate further configurations of an inflation pressure regulator 64. In FIG. 12, the inflation pressure regulator 64 may comprise a pressure relief valve 70 coupled to the second chamber 14. The pressure relief valve 70 may be configured to open when the internal pressure within the second chamber 14 (and hence also the first chamber 12) exceeds a pressure relief threshold value. The pressure relief value 70 may open to relieve any over pressure. The valve 70 may close when the pressure drops below the threshold value. Venting the fluid from the second chamber 14 rather than the first chamber 12 may allow the fluid to be vented outside the body and not inside the stoma 16. This embodiment may be used with, or without, the non-return valve 60 described previously.

In FIG. 13, the inflation pressure regulator 64 may comprise a rupturable portion 72 of the second chamber 14. The rupturable portion 72 may be pressure responsive, and may be configured to rupture when the pressure within the second chamber 14 exceeds a rupture-threshold value. As in the embodiment of FIG. 12, the rupturable portion 72 may vent fluid from the second chamber 14 which can avoid fluid being vented internally in the stoma 12. This embodiment may employ the non-return valve 60 described previously, for ensuring that the rupture in the second chamber 14 does not cause fluid to leak away from the first chamber 12.

In FIG. 14, the inflation pressure regulator 64 may comprise a stop-valve 74 between the first and second chambers. The valve 74 may be configured to shut when the internal pressure in the second chamber 14 reaches or exceeds a threshold. Additionally or alternatively, the valve 74 may be configured to shut when the internal pressure in the first chamber 12 reaches or exceeds a threshold. The valve 74 when closed may function to prevent further inflation fluid from entering the first chamber 12. The valve 74 may be used in combination with, or may incorporate, the non-return valve 60 described previously.

Although various features of the above embodiments have been described in isolation, any of the above features may be combined together, as desired.

An advantage of the invention, particularly as described in the preferred embodiments, is that the inflation fluid 18 may be prepacked inside the plug 10. There may be no need for a separate inflation mechanism or pump. The plug 10 is settable in its deployed condition by manipulating the second chamber 14 to transfer the inflation fluid into the first chamber 12.

The foregoing description is merely illustrative of preferred forms of the invention. Many modifications, improvements and equivalents may be used within the scope and/or spirit of the invention.

The invention claimed is:

1. An ostomy plug comprising:
   a. a first chamber for insertion into a stoma;
   b. a second chamber in fluid communication with the first chamber to enable fluid from the second chamber to inflate the first chamber;
   c. a flatus vent channel incorporated as an internal passage within at least one of the first or second chambers for venting flatus, wherein the first chamber is configured, when inflated, to (i) obstruct escape of solid and/or liquid body waste from the stoma; and (ii} permit venting of flatus from the stoma at an interface between the first chamber and a wall of the stoma.

2. The ostomy plug according to claim 1, wherein the plug further comprises a third chamber disposed around at least a part of the first chamber, and wherein a flatus vent is arranged at an interface between the first and third chambers.

3. The ostomy plug according to claim 1, wherein a flatus vent is defined by a surface texture of the first chamber.

4. The ostomy plug of claim 1, wherein adjacent ends of the first and second chambers are coupled to each other at a junction region.

5. The ostomy plug according to claim 4, wherein the second chamber is detachable from the first chamber after inflation of the first chamber.

6. The ostomy plug according to claim 4, wherein a fluid communication path extends between a first region of the first chamber at or near to the junction region to a second region of the second chamber at or near the junction region.

7. The ostomy plug according to claim 4, wherein the first and second chambers together have a figure-of-eight configuration.

8. The ostomy plug according to claim 4, wherein at least one of the first and second chambers has a convex shape.

9. The ostomy plug according to claim 4, wherein the inflation pressure in the first chamber is controlled by the amount of fluid transferred from the second chamber to the first chamber.

10. The ostomy plug according to claim 4, wherein said valve means includes a pressure relief valve located in or connected to the second chamber.

11. The ostomy plug according to claim 4, further comprising a cover for covering the second chamber, the cover being attachable directly or indirectly to the peristomal skin.

12. The ostomy plug according to claim 11, wherein the cover is a rigid component.

13. The ostomy plug according to claim 11, wherein the cover is a non-rigid elastomeric component.

14. The ostomy plug according to claim 11, wherein the cover is made of flexible film.

15. The ostomy plug according to claim 11, wherein the inflation pressure in the first chamber is controlled by a compression force exerted on the second chamber by the cover.

16. The ostomy plug according to claim 4, further comprising a collar at the junction region, the collar being more rigid than the first and second chambers.

17. The ostomy plug according to claim 4, further comprising an insertion member at the junction region, the insertion member being more rigid than the first and second chambers.

18. The ostomy plug according to claim 17, wherein the insertion member comprises a tube.

19. The ostomy plug according to claim 17, wherein the insertion member is sized and tapered at its proximal end to connect with the stoma opening.

20. The ostomy plug according to claim 17, wherein the first chamber is inverted and stored at least partly within the insertion member prior to inflation of the first chamber.

21. The ostomy plug according to claim 17, wherein the first chamber is inverted and stored at least partly within the second chamber prior to inflation of the first chamber.

22. An ostomy plug comprising:
 a. a first chamber for insertion into a stoma;
 b. a second chamber in fluid communication with the first chamber to enable fluid from the second chamber to inflate the first chamber; said first and second chambers having adjacent ends coupled to each other at a junction region;
 c. a flatus vent channel incorporated as an internal passage within at least one of the first or second chambers for venting flatus, wherein the first chamber is configured, when inflated, to (i) obstruct escape of solid and/or liquid body waste from the stoma; and (ii} permit venting of flatus from the stoma; and
 d. valve means for controlling pressure in the first chamber, said valve means preventing fluid communication between the first and second chambers when the pressure in the first chamber reaches a specific value.

23. An ostomy plug comprising:
 a. a first chamber for insertion into a stoma;
 b. a second chamber in fluid communication with the first chamber to enable fluid from the second chamber to inflate the first chamber; said first and second chambers having adjacent ends coupled to each other at a junction region;
 c. a flatus vent channel incorporated as an internal passage within at least one of the first or second chambers for venting flatus, wherein the first chamber is configured, when inflated, to (i) obstruct escape of solid and/or liquid body waste from the stoma; and (ii} permit venting of flatus from the stoma; and
 d. rupturable means for controlling the inflation pressure in the first chamber, said rupturable means being located in said second chamber and capable of rupturing the second chamber when the pressure in the second chamber reaches a specified value.

24. An ostomy plug comprising:
 a first chamber for insertion into a stoma;
 a second chamber in fluid communication with the first chamber to enable fluid from the second chamber to inflate the first chamber;
 a third chamber for insertion into the stoma; and
 a fourth chamber in fluid communication with the third chamber to enable fluid from the fourth chamber to inflate the third chamber.

25. The ostomy plug according to claim 24, wherein the third chamber is disposed around at least a part of the first chamber.

26. The ostomy plug according to claim 24, wherein the fourth chamber is disposed around at least a part of the second chamber.

27. The ostomy plug according claim 24, wherein the second and fourth chambers are manipulable substantially at the same time to inflate the first and third chambers together.

28. The ostomy plug according to claim 24, wherein the third chamber is inflateable to a different pressure from the first chamber.

29. The ostomy plug according to claim 24, wherein the third chamber has a different surface characteristic from an exposed portion of the first chamber.

30. The ostomy plug according to claim 24, further comprising a flatus vent passage defined at an interface between the first and third chambers.

31. An ostomy plug comprising a first chamber for insertion into a stoma, and a second chamber in fluid communication with the first chamber to enable fluid from the second chamber to inflate the first chamber, wherein the first chamber comprises a non-smooth surface portion for engaging a wall of the stoma.

32. The ostomy plug according to claim 31, wherein the first chamber has a surface portion embossed with a pattern of ridges and valleys.

33. The ostomy plug according to claim 31, wherein the first chamber has a surface portion carrying a plurality of ribs or flap projections.

34. The ostomy plug according to claim 31, wherein the non-smooth surface portion is configured to enhance frictional engagement between the first chamber and a wall of the stoma.

35. The ostomy plug according to claim 31, wherein the non-smooth surface portion is configured to enhance a seal between the first chamber and a wall of the stoma.

36. The ostomy plug according to claim 31, wherein the non-smooth surface portion is configured to enhance venting of flatus around the first chamber.

37. The ostomy plug according to claim 31, wherein the non-smooth surface portion has a microstructure.

38. The ostomy plug of claim 31, wherein at least a portion of the plug carries a surface coating selected from one or more of the group consisting of: a lubricant; a hydrophobic material; a hydrophilic material; and an adhesive.

39. The ostomy plug according to claim 38, wherein said portion of the plug is at least a portion of the first chamber.

40. The ostomy plug of claim 31 further comprising a frangible region for enabling at least a major part of the second chamber to be permanently detached from the first chamber after the first chamber has been inflated.

41. The ostomy plug according to claim 31, further comprising a valve between the first and second chambers, the valve being configured to admit fluid from the second chamber into the first chamber, and to obstruct fluid flow out of the first chamber.

42. The ostomy plug of claim 31 further comprising:
 an insertion aid member, the insertion aid member being more rigid than the first and second chambers, wherein in a non-deployed condition of the plug, the first chamber is substantially deflated and does not protrude substantially from the insertion aid member.

43. The ostomy plug of claim 42, wherein the insertion aid member is disposed at a junction region between the first and second chambers.

44. The ostomy plug of claim 42, wherein the insertion aid member includes a portion that is selected from the group consisting of: a tube; a sleeve; and a collar.

45. The ostomy plug of claim 42, wherein the insertion aid member has an opening that is inwardly tapered for guiding the first chamber into the stoma during inflation of the first chamber.

46. The ostomy plug of claim 42, wherein, in said non-deployed condition, the first chamber is stowed at least partly in the insertion aid member.

47. The ostomy plug of claim 42, wherein, in said non-deployed condition, the first chamber is stowed at least partly in the second chamber.

48. The ostomy plug of claim 42, wherein the insertion aid member is dimensioned to be presented to a stoma without entry of the insertion aid member into the stoma.

49. The ostomy plug of claim 31 further comprising
a fluid control valve.

50. The ostomy plug according to claim 49, wherein the fluid control valve is disposed in the fluid communication path between the first and second chambers.

51. The ostomy plug according to claim 50, wherein the fluid control valve is configured as an inflation retention device for retaining inflation pressure in the first chamber once the first chamber has been inflated.

52. The ostomy plug according to claim 51, wherein the fluid Control valve is configured to admit fluid flow from the second chamber to the first chamber, and to obstruct fluid flow from the first chamber to the second chamber.

53. The ostomy plug according to claim 50, wherein the fluid control valve is responsive to fluid pressure.

54. The ostomy plug according to claim 49, wherein the fluid control valve is configured as an inflation pressure regulator for regulating the inflation pressure of the first chamber.

55. The ostomy plug according to claim 54, wherein the fluid control valve is configured to shut the fluid communication path between the first and second chambers when the pressure in the first chamber exceeds a shut-off threshold.

56. The ostomy plug according to claim 54, wherein the fluid control valve is configured to shut the fluid communication path between the first and second chambers when the pressure in the second chamber exceeds a shut-off threshold.

57. The ostomy plug according to claim 54, wherein the fluid control valve comprises a pressure relief valve for venting fluid when the internal pressure exceeds a pressure relief threshold.

58. The ostomy plug according to claim 57, wherein the pressure relief valve is configured to vent fluid from the second chamber.

59. The ostomy plug of claim 31 further comprising
an inflation regulation device for regulating the fluid pressure to which the first chamber is inflated in use.

60. The ostomy plug according to claim 59, wherein the inflation regulation device comprises a member for pressing against the second chamber for generating a predetermined pressure therein.

61. The ostomy plug according to claim 59, wherein the inflation regulation device comprises a cover for the plug.

62. The ostomy plug according to claim 59, wherein the inflation regulation device comprises a fluid control Valve.

63. The ostomy plug according to claim 62, wherein the fluid control valve is responsive to fluid pressure.

64. The ostomy plug according to claim 62, wherein the fluid control valve is configured to shut the fluid communication path between the first and second chambers when the fluid pressure exceeds a predetermined threshold.

65. The ostomy plug according to claim 62, wherein the fluid control valve is configured as a pressure relief valve for venting fluid when the fluid pressure exceeds a pressure relief threshold.

66. The ostomy plug according to claim 59, wherein the inflation regulation device comprises a rupturable portion for venting pressure from the second chamber when the fluid pressure in the second chamber exceeds a rupture threshold.

\* \* \* \* \*